(12) United States Patent
Mayr et al.

(10) Patent No.: US 9,522,050 B2
(45) Date of Patent: Dec. 20, 2016

(54) PROCESS FOR PRODUCING A DENTAL ARTICLE, ARTICLE OBTAINABLE BY THIS PROCESS AND USES THEREOF

(75) Inventors: Helmar Mayr, Kaufering (DE); Malte Korten, Gröbenzell (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 799 days.

(21) Appl. No.: 13/884,003

(22) PCT Filed: Nov. 7, 2011

(86) PCT No.: PCT/US2011/059496
§ 371 (c)(1),
(2), (4) Date: May 8, 2013

(87) PCT Pub. No.: WO2012/064620
PCT Pub. Date: May 18, 2012

(65) Prior Publication Data
US 2013/0224688 A1 Aug. 29, 2013

(30) Foreign Application Priority Data

Nov. 9, 2010 (EP) .................................. 10190455

(51) Int. Cl.
*A61C 13/00* (2006.01)
*A61C 5/10* (2006.01)
(Continued)

(52) U.S. Cl.
CPC .................. *A61C 5/10* (2013.01); *A61C 8/005* (2013.01); *A61C 8/0013* (2013.01);
(Continued)

(58) Field of Classification Search
CPC ............ A61C 13/0013; A61C 13/0018; A61C 13/0019
(Continued)

(56) References Cited

U.S. PATENT DOCUMENTS 5,902,441 A    5/1999  Bredt
6,121,175 A    9/2000  Drescher
(Continued)

FOREIGN PATENT DOCUMENTS

DE    60112245    3/2006
EP    0 431 924   6/1991
(Continued)

OTHER PUBLICATIONS

Ebert, Direct Inkjet Printing of Dental Prostheses Made of Zirconia, Journal of Dental Research, vol. 88, No. 7, 2009, pp. 673-676.
(Continued)

*Primary Examiner* — Christina Johnson
*Assistant Examiner* — Xue Liu (57) ABSTRACT

In one aspect the present disclosure relates to a process for producing a dental article comprising at least two parts, Part A (e.g. coping) and Part B (e.g. veneer), Part A and Part B each having a 3-dim. structure and an outer and an inner surface, the outer surface of Part A having a shape which essentially corresponds to the shape of the inner surface of Part B, Part B comprising a material with a porous section and being produced with the aid of a rapid-prototyping technique, the process comprising a first heating step, wherein Part A is serving as support structure for Part B during said heating step.

8 Claims, 2 Drawing Sheets

(51) Int. Cl.
*A61C 8/00* (2006.01)
*A61C 13/01* (2006.01)
*A61C 5/00* (2006.01)

(52) U.S. Cl.
CPC ........ *A61C 13/001* (2013.01); *A61C 13/0004* (2013.01); *A61C 13/0006* (2013.01); *A61C 13/0009* (2013.01); *A61C 13/0012* (2013.01); *A61C 13/0013* (2013.01); *A61C 13/0018* (2013.01); *A61C 13/0019* (2013.01); *A61C 13/0022* (2013.01); *A61C 13/01* (2013.01); *A61C 5/002* (2013.01)

(58) Field of Classification Search
USPC ... 264/19, 16, 401, 497, 413, 414, 430, 460, 264/109
See application file for complete search history.

(56) References Cited

U.S. PATENT DOCUMENTS

| | | | |
|---|---|---|---|
| 6,306,784 | B1 | 10/2001 | Drescher |
| 6,322,728 | B1 | 11/2001 | Brodkin |
| 6,648,645 | B1 | 11/2003 | MacDougald |
| 6,955,776 | B1 | 10/2005 | Feenstra |
| 6,994,549 | B2 | 2/2006 | Brodkin |
| 7,086,863 | B2 | 8/2006 | Van der Zel |
| 7,452,836 | B2 | 11/2008 | Apel |
| 7,481,647 | B2 * | 1/2009 | Sambu ............... A61C 13/0013 264/113 |
| 2002/0125592 | A1 | 9/2002 | Schulman |
| 2005/0023710 | A1 | 2/2005 | Brodkin |
| 2006/0099552 | A1 | 5/2006 | Van der Zel |
| 2006/0131770 | A1 | 6/2006 | Dierkes |
| 2008/0241798 | A1 | 10/2008 | Holzner |
| 2008/0318189 | A1 | 12/2008 | Brodkin |
| 2009/0026643 | A1* | 1/2009 | Wiest ..................... A61C 13/09 264/16 |
| 2010/0040767 | A1 | 2/2010 | Uibel |

FOREIGN PATENT DOCUMENTS

| | | |
|---|---|---|
| EP | 2 151 214 | 2/2010 |
| EP | 2 236 121 | 10/2010 |
| WO | WO 94/19112 | 9/1994 |
| WO | WO 03/066326 | 8/2003 |
| WO | WO 2004/073961 | 9/2004 |
| WO | WO 2008/144342 | 11/2008 |
| WO | WO 2009/073498 | 6/2009 |

OTHER PUBLICATIONS

Gbureck, Preparation of tricalcium phosphate/calcium pyrophosphate structures via rapid prototyping, Journal of Materials Science, Materials in Medicine, vol. 19, No. 4, Apr. 2008, pp. 1559-1563.
Moon, Ink-Jet Printing of Binders for Ceramic Components, Journal of the American Ceramic Society, vol. 85, No. 4, Apr. 2002, pp. 755-762.
Seitz, Three-Dimensional Printing of Porous Ceramic Scaffolds for Bone Tissue Engineering, Journal of Biomedical Materials Research, Part B, Appl Biomaterils, 2005, pp. 782-788.
Wang, Solid Freeform Fabrication of Permanent Dental Restorations via Slurry Micro-Extrusion, Journal of the America Ceramic Society, vol. 89, No. 1, Jan. 2006, pp. 346-349.

* cited by examiner

PROCESS FOR PRODUCING A DENTAL ARTICLE, ARTICLE OBTAINABLE BY THIS PROCESS AND USES THEREOF

CROSS REFERENCE TO RELATED APPLICATIONS

This application is a national stage filing under 35 U.S.C. 371 of International Application No. PCT/US2011/059496, filed Nov. 7, 2011, which claims priority to European Application No. 10190455.5, filed Nov. 9, 2010. The disclosures of both applications are incorporated by reference in their entirety herein.

FIELD OF THE INVENTION

The invention relates to a process for producing a dental article using a rapid-protoyping technique and at least one heating step.

BACKGROUND ART

Dental articles like crown and bridges can be produced by different processes using different materials. In the last couple of years a lot of efforts were spent in developing processes for producing dental articles based on ceramic materials. Those dental articles typically comprise two sections, a base section or support structure which provides the necessary strength and a cover section or veneer which should contribute to improving the aesthetic appearance of the final dental article.

The veneering of the support structure is typically done manually (e.g. by layering of ceramic slurries).

Alternatively, the veneering can be done by making a mould and using a pressing technique. Such a process is described e.g. in US 2006/0099552 (van der Zel et al.).

Another approach for producing ceramic dental article is using milling techniques.

WO 2008/144342 (3M) for example relates i.a. to a method of making a facing for a dental restoration comprising the step of providing a facing precursor from which the facing is obtainable and wherein the facing precursor is comprised of an open-celled material. The method provides for efficient manufacturing of dental restorations.

Other references try to produce dental articles applying solid free-forming fabrication methods, however without focusing on dental veneers.

U.S. Pat. No. 5,902,441 (Bredt et al.) focuses on a method of three dimensional printing an article using adhesive particulate mixtures.

U.S. Pat. No. 6,322,728 (Brodkin et al.) deals with mass production of dental restorations by solid free-form fabrication methods.

U.S. Pat. No. 6,955,776 (Feenstra) describes a method for fabricating a functional dental element such as a crown using a three-dimensional printing technique.

U.S. Pat. No. 7,086,863 (Van der Zel) relates to a method for production of an artificial tooth comprising a base layer and at least one cover layer. The method comprises steps like establishing the available outer shape and dimensions for the finished artificial tooth, acquiring an image, determining variations in the appearance determining properties of the cover layer, constructing the base layer and applying the cover layer over the base layer.

U.S. Pat. No. 6,648,645 (MacDougald et al.) relates to a process for fabricating a dental material comprising mixing ceramic powder and one or more media together to form a putty, applying the putty to a model to conform to the shape of the model and to form a ceramic core material; and sintering the model with the putty thereon for a certain period of time.

US 2006/0131770 (Dierkers et al.) describes a process for the production of a dental model with the steps: providing a fluid, solidifiable material and an electrically conductive substance, producing the dental model by rapid prototyping so that the dental model produced is electrically conductive.

WO 2009/073498 (3M IPC) deals with a method comprising positioning a stem in a base, rotating the base and depositing a material on the stem under computer control to create a workpiece.

DESCRIPTION OF THE INVENTION

However, there is still room for improvement especially with regard to the requirements to be fulfilled with respect to modern dental materials.

Moreover, there is a need for a process which allows the manufacturing of ceramic articles, especially dental articles in an easy and efficient way.

In one embodiment the present invention features a process for producing a dental article comprising at least two parts, Part A (e.g. coping or support structure) and Part B (e.g. veneer or facing), Part A and Part B each having a 3-dim. structure and an outer and an inner surface, the outer surface of Part A having a shape which essentially corresponds to the shape of the inner surface of Part B, Part B comprising a material with a porous section and being produced with the aid of a rapid-prototyping technique (RPT technique), the process comprising a first heating step, wherein Part A is serving as support structure for Part B during said heating step.

The invention also relates to an article obtainable by a process as described in the present text.

More particularly, the invention relates to a process for producing a dental article comprising at least two parts, Part A and Part B, Part A and Part B each having a 3-dim. structure and an outer and an inner surface, the outer surface of Part A having a shape which essentially corresponds to the shape of the inner surface of Part B, Part A having the shape of a dental coping and comprising a metal, a metal alloy or a metal oxide containing material, Part B having the shape of a dental veneer and comprising a glass or glass ceramic material, Part B comprising a material with a porous section and being produced with the aid of a rapid-prototyping technique, usually without using Part A, the process comprising a heating step, wherein Part A is serving as support structure for Part B during said heating step and a removing step, wherein Part B is removed from Part A after the heating step, and optionally a fusing step, wherein Part A and Part B are fused together optimally using a fusing composition.

Moreover, the invention features the use of a composition comprising a surface coated powder in a process as described in the present text.

Further, the invention relates to the use of Part A as support structure for Part B during a heating step.

The process described in the present text has some benefits.

It allows the production of a dental article in an efficient manner. Instead of removing material from an existing block using a milling technique, the article is manufactured with the aid of a rapid-prototyping technique. This can save manufacturing time. Moreover, compared to a milling process, overall typically less material is needed for producing the ceramic body. Initially provided material which has not been used during the RPT technique can be re-used, if desired.

It has also been observed that conducting the heating step in the manner described in the present text facilitates the production of 3-dim. structures with less sinter deformation.

Heating Part B comprising a porous material without a support structure may cause Part B to change its dimensions in such a way that Part B does not fit in the desired way to Part A of the ceramic body. This issue can be addressed with the inventive process.

The described process is in particular useful, if small ceramic bodies (referred to as Part B) are to be sintered, which after sintering are to be matted or attached to another article (referred to as Part A). The term "small" means either small in volume or small in wall thickness.

It was also found that Part B can be removed from Part A after a (e.g. first) sintering step, if desired, especially in those cases where there are no undercuts.

Moreover, in case Part A and Part B are needed for a further production process it is typically beneficial if both parts are kept together in the process workflow. This typically simplifies the "tracking process" of the individual parts.

For example in the dental area, Part A can be a high strength support structure and Part B can be a dental veneer or dental facing used for providing a desired appearance to the dental restoration. Until now, the veneering of the support structure was typically done manually by applying multiple layers on the outer surface of the support structure and firing the individual layers. The process described in the present invention simplifies this labour-intensive process.

Thus, the invention enables quick and cheap manufacturing of dental parts in nearly every shape and size. It allows mass manufacturing as well as individual, customized dental parts, if desired.

Unless otherwise specified, within the context of the text of the invention, the following terms have the following meanings.

A "powder" means a dry, bulk solid composed of a large number of very fine particles that may flow freely when shaken or tilted.

A "particle" means a substance being a solid having a shape which can be geometrically determined. The shape can be regular or irregular. Particles can typically be analysed with respect to e.g. grain size and grain size distribution.

A "surface coated powder" is to be understood as a powder comprising individual particles the surface(s) of which bear(s) a further component being different from the material the particle consists of.

A "support structure" is to be understood as a structure being suitable to support or stabilize another article.

The term "dental article" means any article which can and is to be used in the dental field, especially dental restorations and parts thereof. Dental restorations typically comprise at least two parts: a dental support structure (sometimes also referred to as frame or coping) and a dental facing.

The material a dental article is made of should not be detrimental to the patient's health and thus free of hazardous and toxic components being able to migrate out of the article. Examples of dental articles include crowns, bridges, facings (sometimes also referred to as veneers), abutments, and mill blanks. Dental articles are typically of small size and may comprise sections having a wall thickness in the range of about 100 μm to 1000 μm or in the range of about 100 mm to about 500 μm. The total volume of a dental article is typically below about 100 ml or below about 50 ml or below about 10 ml or below about 5 ml.

A "dental support structure" is to be understood as the part of a dental restoration which is typically adhered to a tooth stump or inserted into the patients mouth and suitable for being veneered by a dental facing or dental veneer. A dental support structure has typically sufficient strength to withstand chewing forces.

Dental support structures are typically made of or comprise oxide ceramic materials including $ZrO_2$, and $Al_2O_3$, metals or alloys. Compared to other framework such as pottery or paving stones, the dental framework is small and filigree and of high strength. The thickness of the dental framework can vary from very thin, e.g. at the edges and rims (below about 0.1 mm) to considerably thick, e.g. in the biting area (up to about 7 mm). However, dental frameworks may also be made of or comprise metal or metal alloys.

The term "dental facing" or "dental veneer" refers to the aesthetic part of a dental restoration, meaning the part comprising an outer surface of the finished restoration. The dental facing is further adapted to be applied to a frame or dental support structure which forms another part of the dental restoration, and the dental restoration is in turn applied to a tooth. The dental facing is preferably arranged at those parts of the dental support structure that are likely to be visible in a patient's mouth, or that in particular functionally co-operate with the adjacent or opposed teeth of a patient, for example.

Dental veneers are also small and filigree objects. The strength of dental veneers, however, is typically less compared to dental frameworks. Dental veneers are typically made of or comprise glass or glass ceramic materials.

A dental support structure or a dental veneer usually has a 3-dimensional inner and outer surface including convex and concave structures. The outer surface of the dental framework typically corresponds essentially to the inner surface of the dental veneer. The inner surface of the dental framework typically corresponds essentially to the outer surface of a prepared tooth stump, whereas the outer surface of the dental veneer typically corresponds essentially to the final dental restoration.

"Glass" means an inorganic non-metallic amorphous material. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former.

"Glass-ceramic" means an inorganic non-metallic material where one or more crystalline phases are surrounded by a glassy phase so that the material comprises a glass material and a ceramic material in a combination or mixture. Thus, a glass ceramic is a material sharing many properties with both glass and crystalline ceramics. Usually, it is formed as a glass, and then made to crystallize partly by heat treatment. So, glass ceramics are made of a glassy phase with crystals, which typically have no pores in the glassy phase or between crystals. Glass ceramics mainly refer to a mixture of lithium-, silicon-, and aluminum-oxides.

"Ceramic" means an inorganic non-metallic material that is produced by application of heat. Ceramics are usually hard, porous and brittle and, in contrast to glasses or glass ceramics, display an essentially purely crystalline structure.

A "ceramic article" is to be understood as an article comprising a ceramic, glass or glass ceramic material.

"Sintering" means making objects from a powder, by heating the material (typically below its melting point-solid state sintering) until its particles adhere to each other.

"Density" means the ratio of mass to volume of an object. The unit of density is typically g/cm$^3$. The density of an object can be calculated e.g. by determining its volume (e.g. by calculation or applying the Archimedes principle or method) and measuring its mass.

The terms "sintering" or "firing" are used interchangeably. A pre-sintered ceramic framework shrinks during a sintering step, that is, if an adequate temperature is applied. The sintering temperature to be applied depends on the ceramic material chosen. For $ZrO_2$ based ceramics a typical sintering temperature range is about 1200° C. to about 1600° C. $Al_2O_3$ based ceramics are typically sintered in a temperature range of about 1300° C. to about 1700° C. Glass ceramic materials are typically sintered in a range of about 700 to about 1100° C. for about 0.1 to about 3 h.

Sintering typically includes the densification of a porous material to a less porous material (or a material having less cells) having a higher density, in some cases sintering may also include changes of the material phase composition (for example, a partial conversion of an amorphous phase toward a crystalline phase).

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field.

The material structure categories "open-celled" and "closed-celled" can be determined for different porosities measured at different material samples (e.g. using mercury "Poremaster 60-GT" from Quantachrome Inc., USA) according to DIN 66133. A material having an open-celled or open-porous structure can be passed through by e.g. gases. A "porous material" relates to a material which contains open or closed cells and which can be condensed, e.g. by a sintering or heating process. A porous material is typically also able to absorb a liquid, if desired. The liquid is typically able to migrate into the pores of the material and remains at least to some extend (typically depending on the amount of liquid used) in these pores, even if the material is removed from the liquid.

The structure of a material as referred to in this specification may be categorized as "open-celled", "closed-celled" and "generally free of cells".

The term "open-celled" relates to an "open porosity" according to the mercury porosimetry as defined in DIN 66133. Typical values are between about 6% and about 35%, of between about 15% and about 35%, or between about 30% and about 35%.

The term "closed-celled" relates to a "closed porosity". Closed cells are those cells which are not accessible from the outside and cannot be infiltrated by gases under ambient conditions.

The unit "cells per mm$^2$" is related to the number of cells present on a cross section of the sample to be analysed. A suitable test method is given in DIN 13925.

The volume of a sample can be determined based on the overall outer dimensions of the sample. The density of the sample can be calculated from the measured sample volume and the sample mass. The total volume of glass ceramic material can be calculated from the mass of the sample and the density of the used material.

The total volume of cells in the sample was assumed to be the remainder of the sample volume (100% minus the total volume of material).

An article is classified as "absorbent" if the article is able to absorb a certain amount of a liquid, comparable to a sponge. The amount of liquid which can be absorbed depends e.g. on the chemical nature of the article, the viscosity of the solvent, the porosity and pore volume of the article. E.g. a pre-sintered article, that is an article which has not been sintered to full density, is able to absorb a certain amount of liquid. Absorbing of liquids is typically only possible if the article has an open-porous structure.

A composition or solution is "essentially or substantially free of" a certain component within the meaning of the invention, if the composition or solution does not contain said component as an essential feature. Thus, said component is not wilfully added to the composition or solution either as such or in combination with other components or ingredient of other components. A composition being essentially free of a certain component usually contains the component in an amount of less than about 1 wt. % or less than about 0.1 wt. % or less than about 0.01 wt. % (or less than about 0.05 mol/l solvent or less than about 0.005 mol/l solvent or less than about 0.0005 mol/l solvent) with respect to the whole composition. Ideally the composition or solution does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION

The invention features a process for producing a ceramic body comprising at least two parts, Part A and Part B.

Both parts have a 3-dimensional (3-dim.) structure and an outer and an inner surface. The shape of the outer surface is typically overall convex, whereas the shape of the inner surface is typically overall concave.

The outer surface of Part A has a shape which essentially fits or corresponds to the shape of the inner surface of Part B. Thus, if desired, Part A and Part B can be matted together.

The term "essentially fits or corresponds to" means that the shape of the (corresponding) surfaces are nearly identical but allow for small deviations comparable to the overall size of the article. The shapes of the surfaces are typically such that both surfaces can be matched together.

According to one embodiment, the deviations in shape may be such that a fusing composition can be applied between the two surfaces, if desired.

A gap for receiving a fusing composition may be in the range from about 100 µm to about 500 µm or from about 150 µm to about 400 µm or from about 200 µm to about 300 µm.

In the dental field, Part A may also be referred to as dental coping or dental support structure. Part B may be referred to as dental veneer or dental facing.

The materials Part A and Part B are made from or comprised of can be the same or different.

The inventive process further comprises a heating step. The heating step typically causes Part B to partially sinter. That is, Part B comprising a porous section before the heating step is applied, partially changes its dimensions during the heating step.

Moreover, during the heating step Part A serves as support structure for Part B and thus stabilizes the shape of Part B.

During the heating step organic residues (e.g. stabilizers, binders) which may be present in the material Part B is made of, are typically removed. Besides from that or in addition to that the strength of the structure of Part B is increased. Moreover, with Part A acting or functioning as a support structure during the heating step, the shape of Part B and the fitting accuracy of Part B is essentially maintained or at least not negatively affected.

The material Part A is made of is not particularly limited. Every kind of material can be used provided it is suitable for supporting Part B during a heating step.

According to one embodiment Part A comprises, essentially consists of or consists of a ceramic material, metal or combinations thereof.

According to another embodiment, Part A can be characterized by at least one of the following parameters:

coefficient of thermal expansion: from about $8*10^{-6}$ $K^{-1}$ to about $20*10^{-6}$ $K^{-1}$, the material density of the dental support structure being in a range of from about 3.5 g/cm$^3$ to about 19 g/cm$^3$ or from about 5 g/cm$^3$ to about 10 g/cm$^3$ or from about 5 g/cm$^3$ to about 7 g/cm$^3$.

Typical ceramic materials which can be used include oxides of zirconium, aluminum, titanium and combinations thereof.

With respect to zirconia, yttrium doped tetragonal stabilized zirconia can be preferred. This material is often also referred to as YTZP and commercially available from e.g. Tosoh Comp., Japan.

Part A, however, can also comprise, essentially consists of or consists of a metal or metal alloy.

Suitable metals can be characterized by at least one of the following features:

Coefficient of thermal expansion of the metal the metallic frame is made of typically ranges from about $9.6*10^{-6}$ $K^{-1}$ to about $17.3*10^{-6}$ $K^{-1}$. Other suitable ranges include from about $9.6*10^{-6}$ $K^{-1}$ to about $15.2*10^{-6}$ $K^{-1}$ and $13.8*10^{-6}$ $K^-$ to about $15.2*10^{-6}$ $K^{-1}$ and $16*10^{-6}$ $K^{-1}$ to about $17.3*10^{-6}$ $K^{-1}$.

Being selected from the group consisting of Ti, Au, Pt, Pd, Ag, Zn, Co, Cr, Mo, W, Ni, Fe and combinations and alloys thereof.

Suitable alloys can be obtained from Argen Comp., Wieland Comp., Bego Comp., Dentaurum Comp. and Degu-Dent Comp.

If Part A comprises a ceramic material, the ceramic material is preferably in a sintered stage. According to a further embodiment, the material Part A is made from is non-porous.

Part A is typically made by a milling process. However, if desired, Part A can also be made using a rapid-prototyping technology as described in the present text.

Part B comprises a material with a porous section. The porous section can only be a specific segment of Part B. Alternatively, the material Part B is made of can be completely porous. The porous section typically results from the rapid-prototyping technique which is used for producing Part B.

Part B is produced by a rapid-prototyping technology and can typically be characterized by at least one of the following parameters before a first heating step is conducted:

Density: from about 0.5 to about 1.8 g/cm$^3$ or from about 0.8 to about 1.3 g/cm$^3$;

Raw breaking resistance: from about 0.1 to about 10 MPa or from about 1 to about 5 MPa.

Pore Volume: from about 35 to about 65% or from about 45 to about 55%.

If desired, the density can be determined as follows: using the Archimedes method or calculating the density from mass and volume of the sample.

If desired, the raw breaking resistance can be determined as follows: 3 point bending test according to DIN 6872.

If desired, the pore volume can be determined as follows: porosity or open porosity can be measured using a mercury porosimeter in accordance with DIN 66133 as available under the designation "Poremaster 60-GT" from Quantachrome Inc., USA.

The rapid-prototyping techniques used for producing Part B is not particularly limited unless it is not suitable for producing Part B. Part B is typically produced without making use of Part A. Thus, Part B is typically produced independently from Part A. During production of Part B, Part A does not act as a matrix.

Rapid-prototyping techniques which can be used for producing Part B include ink-jet printing, 3d-printing, multijet plotting, robo-casting, electrophoretic deposition, fused deposition modeling, laminated object manufacturing, selective laser sintering or melting, stereolithography, photostereolithography, or combinations thereof.

Those and other techniques are e.g. described in U.S. Pat. No. 5,902,441 (Bredt et al.), U.S. Pat. No. 6,322,728 (Brodkin et al.) and U.S. Pat. No. 6,955,776 (Feenstra) and U.S. Pat. No. 7,086,863 (Van der Zel).

The disclosure of these patents as it regards the description of rapid-prototyping techniques is herewith incorporated by reference and regarded as part of this application.

Commercially available examples of rapid-prototyping equipment which can be used include printers from ZCorp. company like the printer ZPrinter™ 310 plus.

According to one embodiment, the rapid-prototyping technique makes use of a powder.

The particles in the powder typically have a particle size below about 70 µm or below about 60 µm or below about 25 µm. If desired, the particle size can be measured with laser diffraction. The adjustment of the particle size can be done using a sieve having the desired maximum mesh size.

If larger particles are used for producing the article (e.g. particles having a particle diameter above about 70 µm or above about 80 µm), the surface resolution of the final product might be reduced.

The powder which can be used for producing Part B may comprise a glass and/or glass ceramic material.

The nature and structure of the glass and/or glass ceramic material is not particularly limited unless it is detrimental to the desired performance of the composition.

The glass or glass ceramic material is preferably selected to be compatible for use in human bodies. Furthermore, the glass or glass ceramic material is preferably selected to provide good aesthetic appearance for the dental restoration, in particular when combined with a dental framework.

Glass or glass ceramics materials which can be used can typically be characterized by at least one of the following features:

comprising: 55 wt. % to 75 wt. % of silicon oxide, 8 wt. % to 22 wt. % of aluminum oxide, 0 wt. % to 8 wt. % of boron oxide, 3 wt. % to 12 wt. % of potassium oxide, 4 wt. % to 12 wt. % of sodium oxide, 0 wt. % to 2 wt. % of cerium oxide, 0 wt. % to 2 wt. % of tin oxide, 0 wt. % to 3 wt. % of zinc oxide, 0 wt. % to 4 wt. % of phosphor oxide, 0 wt. % to 3 wt. % of calcium oxide, 0 wt. % to 3 wt. % of lithium oxide, and 0 wt. % to 1 wt. % of fluoride, 0 wt. % to 3 wt. % of lanthanum oxide or lanthanide oxide;

Coefficient of thermal expansion: about $8*10^{-6}$ $K^{-1}$ to about $15.8*10^{-6}$ $K^{-1}$ or $8*10^{-6}$ $K^{-1}$ to about $9*10^{-6}$ $K^{-1}$ or about $12*10^{-6}$ $K^{-1}$ to about $13.6*10^{-6}$ $K^{-1}$ or from about $15*10^{-6}$ $K^{-1}$ to $15.8*10^{-6}$ $K^{-1}$;

melting temperature (range): around or less than about 1000° C.;

density: about 2.0 to about 2.8 or about 2.2 to about 2.6 g/cm$^3$ (according to the technical data sheet provided by the manufacturer) and/or glass transition temperature: about 500 to about 600° C. or about 520 to about 580° C., preferably about 550° C.

Glass or glass ceramic materials which may, for example, be used are generally available under the designations:

"VMK 95" and "Omega 900" from Vita Zahnfabrik, Bad Säckingen, Germany;

"IPS Classic" and "IPS d.Sign" from Ivoclar Vivadent, Liechtenstein;

"Vintage" from Shofu, Japan; and

1"REFLEX" from Wieland GmbH & Co. KG, Pforzheim, Germany.

"VM9" from Vita Zahnfabrik, Bad Säckingen, Germany

"LAVA Ceram" from 3M ESPE, Seefeld, Germany

"Cerabien Zr" from Noritake, Japan

"LM ZrO2" from Chemichl AG, Liechtenstein.

The crystalline phase of the glass ceramic material may also comprise leucit, lithium disilicate, zirconia and/or mica crystallites. Suitable lithium silicate glass ceramic materials are described e.g. in U.S. Pat. No. 7,452,836 B2, U.S. Pat. No. 6,306,784 B1, U.S. Pat. No. 6,121,175. These references are herewith incorporated by reference. A typical composition comprises: $SiO_2$ in an amount of about 55 to about 71 wt. %, $Al_2O_3$ in an amount of about 5 to about 16 wt. %, $B_2O_3$, in an amount of about 0.2 to about 10 wt. %, $K_2O$ in an amount of about 4 to about 10 wt. %, $Na_2O$ in an amount of about 3 to about 14 wt. % and optionally further components selected from CaO, F, $P_2O_5$, $Li_2O$, BaO and ZnO.

The glass and/or glass ceramic material does typically not comprise so-called reactive glass(es), that is, glass(es) which can undergo a neutralization or ion-exchange reaction with acidic substances. Reactive glasses are typically used in glass ionomer cement (GIZ) compositions.

A cement reaction is defined as the reaction of a reactive glass with a polyacid, which results in a hardened product typically within utmost 20 min upon mixing.

Preferred glasses and/or glass ceramic materials to be used according to the present invention comply with the requirements according to EN ISO 6872:2008. In contrast to reactive glasses used in glass ionomer cements, the glasses and/or glass ceramic materials to be used according to the present invention have a reduced solubility in diluted acetic acid, e.g. less than about 100 μg/cm$^2$ (measured according to EN ISO 6872:2008, Table 1, Chapter 7.6).

The glass and/or glass ceramic material may also comprise pigments. Pigments which can be used include the oxides of Cr, Mn, Fe, V, Co, Sb, Ni, Sn, Zn, combination and mixtures thereof. The use or addition of pigments to the composition can be beneficial in that, in particular after a heating or sintering step tooth coloured product(s) can be provided, wherein the term "tooth coloured" refers to the Vita colour scheme known to the person skilled in the art.

In one embodiment the particles of the powder used in the rapid-prototyping process are surface coated.

The process for producing surface coated powder particles is not particularly limited. The particles of the powder are typically brought in contact with a surface coating agent and mixed. The mixture is dried and optionally milled.

According to one embodiment, a powder comprising particles having a particle size in the range from about 10 μm to about 70 μm (d50) or from about 20 μm to about 60 μm is mixed with a surface coating agent.

The surface coating agent may comprise water and a binder.

Binders which can be used include polyvinyl acetate (PVA), starch adhesives, acrlyates, polyvinyl alcohol, polyethylene oxide (PEO), ethylene vinyl acetate (EVA) and mixtures or combinations thereof.

The binder is typically present in the surface coating agent in an amount of about 1 to about 8 wt. % or from about 3 to about 5 wt. %, wt. % with respect to the weight of the surface coating agent.

If the amount of binder used is too high, the particles might already stick together during storage. If the amount of binder used is too low, the particles might not properly adhere together.

After mixing the powder particles with the surface coating agent, the mixture is typically dried and further milled, if desired. Milling can be accomplished with commercially available ball mills. The milled surface coated particles may further be sieved (e.g. through a mesh sieve) to obtain the desired particle distribution. Useful particle sizes include those referred to above when describing the powder.

The nature of the liquid which is typically used in the rapid-prototyping technique is not particularly limited, unless the intended purpose cannot be achieved.

Suitable liquids can be characterized by at least one of the following features:

boiling point: about 60 to about 120° C., freezing point: about −120 to about 0° C., density: about 0.7 to about 1.2 g/cm3, mixable with water, pH-value (if mixed with water): from about 2 to about 10 or from about 4 to about 8.

Specific examples of liquids which can be used include water, alcohols (including methanol, ethanol n- and isopropanol), ketons (including acetone) and mixtures thereof.

If desired, the liquid can comprise one of more colourants. The colourant can be a solid (e.g. pigment) or a soluble substance. Suitable colourants include those mentioned above, but also organic substances which are able to form coloured oxides during a sintering step.

According to one embodiment, the surface coated particles are put in a receptacle of a rapid-prototyping device (sometimes also referred to as powder bed). A smooth surface of the powder is typically produced using a wiper, rake or re-coater.

The liquid is applied through at least one nozzle of the rapid-prototyping device used. The nozzle is typically located in a so-called printing or plotting head similar to well-known ink-jet printing equipment used in daily practice.

A small amount of liquid is applied to at least one section of the layer of the surface coated powder. This at least one section is determined by the software used for controlling the rapid-prototyping device.

The liquid typically interacts with binder located on the surface of the surface coated powder and causes the powder particle to stick or adhere together or react with each other and form a section of the article to be produced.

A further layer of surface coated powder is applied on top of this section and the printing step is repeated as long as needed to produce the article.

The article obtained has typically a porous structure and is sufficiently stable in order to be removed from the powder bed either by hand or with the aid of mechanical equipment.

A suitable process is also described in U.S. Pat. No. 5,902,441 (Brendt et al.).

It is estimated that up to about 250 ceramic bodies (Part B) can be produced within about 1 hour using a commercially available rapid-prototyping device.

The process may comprise one or more additional steps.

The process for producing the ceramic body may comprise a de-bindering or de-binding step. Such a step typically comprises a heating step. In such a step, the binder used for fusing the powder particles together is removed, at least to a certain part. This might be beneficial to increase the strength of the green body before further heating step(s) (e.g. fusing or sintering step) is(are) carried out. Such a step is typically carried out within a temperature range of about 300 to about 500° C. or from about 350 to about 480° C. or from about 400 to about 450° C.

The process may comprise the step of removing Part B from Part A, in particular after a first heating step has been conducted.

The process may comprise the step of fusing Part A to Part B optionally using a fusing composition.

The process may comprise a second heating step, which is typically carried out after the fusing step.

According to a further embodiment, the process may comprise the steps of
a) providing Part A,
b) producing Part B with the aid of a rapid-prototyping technique,
c) conducting a first heating step to Part A and Part B, Part B being located during the heating step on top of Part A,
d) optionally removing Part B from Part A,
e) optionally fusing Part A and Part B using a fusing composition,
f) optionally conducting a second heating step,
wherein step b) can also be conducted before, after or simultaneously with step a).

The first heating step is typically conducted at a temperature which causes the porous material of Part B to at least partially sinter. This typically results in a Part B having an increased strength and hardness.

If desired, the second heating step is typically conducted at a temperature which causes the material of Part B to fully sinter.

The first heating step can typically be characterized by at least one of the following parameters:
Temperature: from about 500 to about 800° C. or from about 600 to about 700° C.;
Duration: from about 15 to about 60 min or from about 25 to about 40 min;
Atmosphere: Air (ambient pressure).

The heating can be done in any suitable furnace. Commercially available furnaces include e.g. Dekema Austromat 3001 and Zubler Vario 300.

During this heating step Part B is supported by Part A. Part A helps to stabilize Part B. Depending on the temperature used, the porous material section of Part B may shrink and thus change its dimensions. This may result in an unwanted deformation of Part B either in length or in height. However, if during this heating step Part B is supported by Part A, unwanted deformation does typically not occur.

As the material used for producing Part B typically comprises a binder material, the heating step can be characterized as a de-bindering step, that is a step, where the binder material is removed.

After the first heating step the material of Part B can typically be characterized by the following parameters:
Density: from about 0.7 to about 2.0 $g/cm^3$ or from about 1 to about 1.5 $g/cm^3$;
Raw breaking resistance: from about 10 to about 50 MPa or from about 25 to about 35 MPa.
Pore Volume: from about 25 to about 55% or from about 35 to about 45%.

The respective parameters can be determined as described above.

Using a fusing composition can be beneficial to increase the bonding strength between the respective surfaces of Part A and Part B. Without a fusing composition it might happen that the individual parts do not adhere sufficiently together. This, however, typically depends also on the geometry of the Parts to be adhered together. Especially for Parts having no suitable retention elements on their surfaces, the use of a fusing composition might be advantageous.

Using a fusing composition can also be beneficial in that it helps improving the fit of the individual parts e.g. by filling small cavities or recesses in the surfaces.

A fusing composition which can be used for fusing Part A and Part B typically comprises water, a glass and/or glass ceramic material and optionally a rheological modifier.

Fusing compositions which can be used are described e.g. in EP 2 236 121 (3M), the disclosure of which is herewith incorporated by reference and regarded as part of this application.

The fusing composition may comprise a rheological modifier. The rheological modifier may have a molecular weight above about 500,000. The fusing composition may also comprise polyethylene glycol, typically with a molecular weight below about 10,000.

According to one embodiment, the fusing composition can be characterized by one or more of the following features:
Viscosity of liquid without glass and/or glass ceramic material: being in the range of about 10 mPas to about 1,000 mPas or being in the range of about 20 mPas to about 500 mPas, or being in the range of about 30 mPas to about 100 mPas measured at 23° C. with a shear rate of 50 $s^{-1}$ (measured with a viscosimeter MCR301 (Anton Paar Comp.), cone plate geometry, diameter 25 mm, temperature of 23° C., shear rates d(gamma)/dt of 50 $s^{-1}$.
Viscosity of the fusing composition (including glass and/or glass ceramic material): being in the range of about 500 to about 20,000 mPas, or about 1000 to about 10,000 mPas or about 1500 to about 5000 mPas.
(If desired, the viscosity measurement can be done a follows: A viscosimeter MCR301 (from Anton Paar Comp.) can be used. A portion of the liquid/powder composition is placed between two steel discs with a diameter of 8 mm and a gap of 1 mm at a temperature of 23° C. The gap is filled completely with the liquid/powder composition. Excess liquid/powder composition is removed. To avoid an undesired drying of the slurry during the measurement a ribbon of wetted paper tissue is laid around the discs in order to raise the humidity. The shear rate between the rotating discs d(gamma)/dt is set constantly to 50 s$^{-1}$. The measurement is done 500 s after starting the shearing process of the composition.)

The composition can be combusted without leaving organic residues, if heated up to a temperature of about 750° C. for about 1 min at ambient pressure (e.g. 1013 mbar).

The content of organic components (containing carbon) is below about 7 wt. % or below about 3 wt. % or below about 2 wt. % with respect to the fusing composition.

The term "can be combusted without leaving residues" means that if about 200 mg of the composition is heated up to a temperature of about 750° C. for about 1 min at ambient pressure, no visible (visible with the human eye) deposits can be found. That is, the composition either evaporates or can be burnt producing only gaseous components including carbon oxide and water. Except for the glass and/or glass ceramic material being present in the composition essentially no further components are left. This can be determined, if desired, e.g. by visually (with the human eye only) inspecting a final dental restoration obtained after a firing step. A greyish appearance of the dental restoration can be an indicator for a dental composition not fulfilling the above mentioned feature. E.g., using a glycerol containing composition typically leads to a dental restoration having a greyish appearance, something which is typically not desirable.

The second heating step, if conducted, can typically be characterized by at least one of the following parameters:
Temperature: from about 600 to about 1000° C. or from about 700 to about 900° C.;
Duration: from about 45 to about 90 min or from about 50 to about 70 min;
Atmosphere: Air and vacuum (e.g. from about 20 to about 200 mbar)

The heating can be done in any suitable furnace. Commercially available furnaces include those which can also be used for performing the first heating step.

Figure 1:
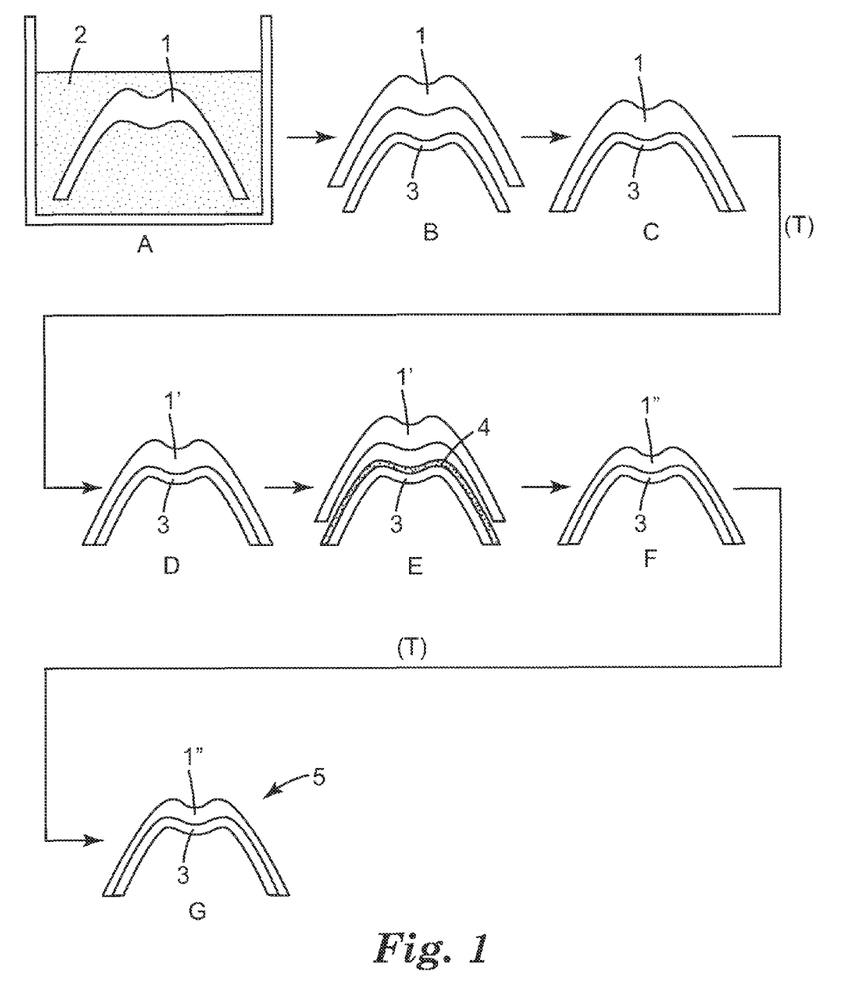
FIG. 1 exemplifies a flow chart of the process described in the text of the invention.

FIG. 1 exemplifies an embodiment of the process described in the present text.

Section A: Part B (1) is located in a powder bed (2). Part B (1) has the shape of a dental facing.

Section B: Part B (1) is located on top of Part A (3). The shapes of the respective surfaces correspond essentially to each other. Part A has the shape of a dental coping.

Section C: Heat is applied to Part A (3) and Part B (1), wherein Part B (1) is supported by Part A (3) during this first heating step.

Section D: The volume of Part B (1') is reduced compared to Section B. The heating treatment caused the material of Part B (1) to shrink (e.g. partially sintering).

Section E: Part B (1') has been removed from Part A (3) and a fusing composition (4) has been introduced between the outer surface of Part A (3) and the inner surface of Part B (1')—these steps are not shown. The result is an arrangement where Part B (1') is located on top of Part A (3) using a fusing composition (4).

Section F: A second heating step is applied to this arrangement.

Section G: A dental restoration (5) is shown. The material of Part B (1') has been fully sintered and is affixed to Part A (3). The fusing composition has partially disappeared and the rest merged with the material of Part B (1").

According to a specific embodiment, the process described in the present text can be characterized as follows:
providing a Part A and producing a Part B with the aid of a rapid-prototyping technique,
Part A having the shape of a dental coping and comprising a zirconia, alumina, titanium oxide, metal or metal alloy containing material,
Part B having the shape of a dental veneer and comprising a glass or glass ceramic material,
conducting a first heating step to Part A and Part B, Part B being located during this heating step on top of Part A,
the first heating step being conducted in a temperature range from about 500 to about 800° C.,
optionally removing Part B from Part A,
optionally fusing Part A and Part B using a fusing composition,
optionally conducting a second heating step,
the second heating step being conducted in a temperature range from about 600 to about 1000° C.,
optionally conducting a finishing or polishing step.

Figure 2:
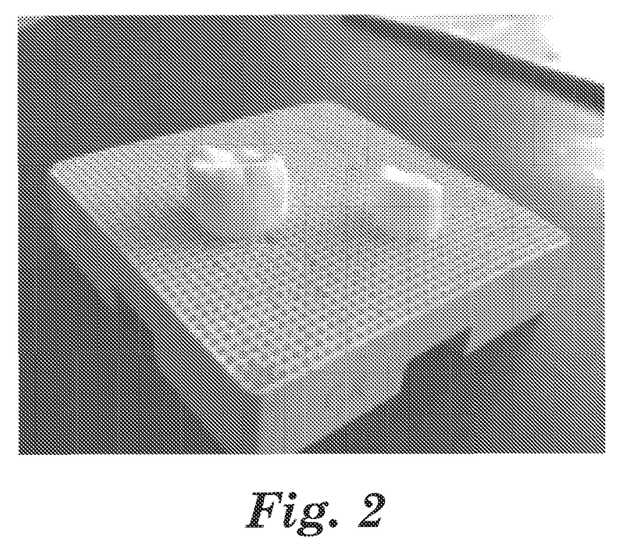
FIG. 2 shows a mesh tray with two ceramic bodies having the shape of a dental crown.
Figure 3:
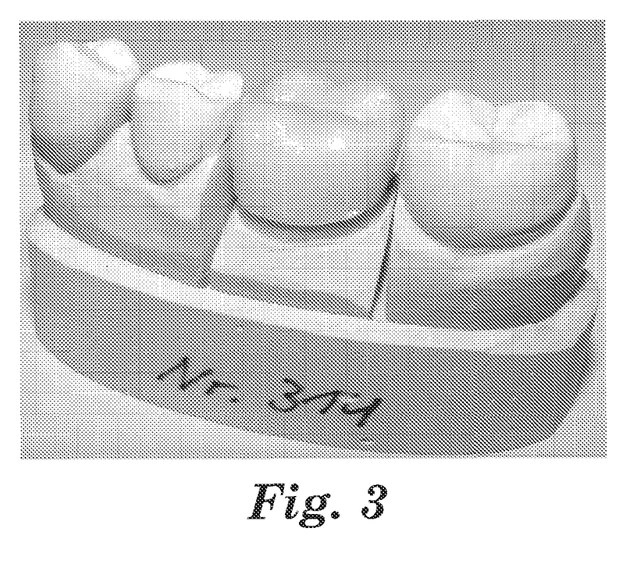
FIG. 3 shows a ceramic body having the shape of a dental crown located on a jaw model.

FIG. 2 and FIG. 3 show real examples of ceramic bodies obtained according to the process described in the present text.

FIG. 2 shows a mesh tray with two ceramic bodies having the shape of a dental crown. The ceramic body shown on the left hand side has been produced by a rapid-prototyping technique and comprises a porous glass and/or glass ceramic material. The ceramic body shown on the right hand side has also been produced by a rapid-prototyping technique. This ceramic body, however, has further been treated with heat wherein the ceramic body was supported during this heating step by a support structure comprising a zirconia material.

FIG. 3 shows a ceramic body having the shape of a dental restoration (dental crown) produced according to the process described in the present text. The dental restoration is located on a jaw model. In addition a glace layer has been applied on the outer surface of the dental restoration (finishing step).

The invention is also directed to an article obtainable or obtained by the process described in the text of the invention.

The shape of the article which can be produced according to the process described in the present text is not particularly limited. A further benefit of using a RP technique can be seen in that shapes comprising undercut sections can be produced, too. This is typically not possible using a milling technique. Moreover, the surface of an article obtainable by a RP technique does not show milling tracks.

If the process is used to produce a dental article, the article (in particular, if the article comprises Part A and Part B as described in the above text) can have the shape of a dental crown, bridge, an abutment for a dental implant, a veneer or a part of either of those articles.

The invention is also directed to a method of using a composition comprising a surface coated powder in a process for producing a dental article, wherein the process comprises the application of a rapid-prototyping technique and a first heating step.

The invention is also directed to the use of a Part A as support structure for a Part B during a first heating step, wherein Part B is located on top of Part A. Part A and Part B are defined as described in the present text.

According to a further embodiment, the invention is directed to a process for producing a dental veneer comprising the steps of a) providing a Part A having a 3-dim. structure and an outer surface, the outer surface of Part A having the shape of a dental coping, b) producing a Part B having a 3-dim. structure and an outer and an inner surface, the outer surface of Part A essentially corresponding to the inner surface of Part B, Part B having the shape of a dental veneer and comprising a material with a porous section and being produced with the aid of a rapid-prototyping technique without using Part A, c) placing Part B with its inner surface on the outer surface of Part A, d) heating Part A and Part B, wherein Part A is serving as support structure for Part B during the heating step, e) removing Part B from Part A after the heating step, wherein step b) can be conducted before, after or simultaneously with step a).

Part A and Part B are as described in the text above.

The process described in the present text does typically not comprise an infiltrations step, even if such a step may not completely be excluded. Another step which is typically not needed any more is a milling step. Part B can be obtained or produced without a milling step.

The following examples are given to illustrate, but not limit, the scope of this invention.

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (23° C.; 1013 mbar).

Measurements

Particle Size

If desired, the mean particle size can be determined using a commercially available granulometer (Laser Diffraction Particle Size Analysis Instrument, MASERSIZER 2000; Malvern Comp.) according to the instruction of use provided by the manufacturer.

Porosity

If desired, the porosity or open porosity can be measured using a mercury porosimeter in accordance with DIN 66133 as available under the designation "Poremaster 60-GT" from Quantachrome Inc., USA.

Viscosity

If desired, the viscosity can be evaluated using a rheometer MCR 300 manufactured by Anton Paar equipped with a 8 mm parallel plate geometry with flat surfaces. The test is typically performed at 23° C. The temperature is controlled within 0.1° C. by a Peltier element in the lower plate. The measurement gap is typically constant at 0.2 mm.

A: Powder Preparation

Glass powder Lava™ Ceram ICE 2 (available from 3M ESPE) was mixed with an aqueous solution containing 20 wt. % polyvinyl acetate (PVA) binder in a speedmixer (Mikronia Technologie AG, Spreitenbach, Switzerland) to obtain a surface coated powder. The mixture was dried and milled in a rotary ball mill with zirconia jar and balls (Retsch, Haan, Germany) for about 60 min. The milled mixture was sieved through a mesh to obtain a mean grain size distribution below about 63 µm.

B: Printing

An STL computer file describing the 3-dim. shape of the article to be produced (e.g. dental veneer) was loaded into the software of the printer (ZCorp 310 plus printer; ZCorporation, Burlington, USA).

The printing was done as described in the instruction for use provided by the manufacturer of the printer, wherein parameters like shrinkage and layer thickness were additionally taken into account.

A water based binder (obtainable from ZCorporation, Burlington, USA) was jetted onto specific sections of the uppermost layer of the powder as calculated by the software of the printer. The binder component on the surface of the powder was partly dissolved. The respective particles stick together. This step was repeated until the shape of the desired article was obtained. After drying the printed article was removed from the powder-bed and excessive powder was removed (e.g. using pressurized air).

C: De-Bindering Step

The article was dried in an oven at about 450° C. for about 180 min in order to remove the binder.

D: Heating Step (I)

The printed article of step C was put on top of a corresponding support structure (e.g. dental coping), which was produced separately. The assembly was heated up to about 650° C. (duration: about 30 min) to increase the strength of the article.

The material of the support structure used was densely sintered zirconia. The pre-sintered article was removed from the support structure. The article obtained is shown on the right hand side of FIG. 2.

E: Fusing and Heating Step (II)

After the pre-sintering step the pre-sintered article was removed from the support structure.

An aqueous fusing composition containing a glass ceramic material (cf. EP 2 236 121; 3M) was applied to the inner surface of the article and the outer surface of the support structure and the respective surfaces were manually matted together.

After a short drying period the two part system was sintered at about 790° C. in a furnace for about 60 min. To the outer surface of the obtained article a glaze layer was applied and a third heat treatment was conducted. The article obtained is shown in FIG. 3.

The invention claimed is:

1. A process for producing a dental article comprising at least two parts, Part A and Part B, Part A and Part B each having a 3-dim. structure and an outer and an inner surface, the outer surface of Part A having a shape which essentially corresponds to the shape of the inner surface of Part B, Part A having the shape of a dental coping and comprising a metal, a metal alloy or a metal oxide containing material, Part B comprising a material with a porous section, being produced with the aid of a rapid-prototyping technique without using Part A, Part B having the shape of a dental veneer and comprising a glass or glass ceramic material, the process comprising a heating step, wherein Part A is serving as support structure for Part B during said heating step and a removing step, wherein Part B is removed from Part A after the heating step, the process comprising steps performed in the following order:

a) conducting a first heating step to Part A and Part B, Part B being located during the first heating step on top of Part A, b) removing Part B from Part A, c) fusing Part A and Part B using a fusing composition, d) conducting a second heating step to Part A fused with Part B,
e) applying a glaze layer to an outer surface of Part B, and
f) conducting a third heating step to Part A fused with Part B and with the applied glaze layer.

2. The process according to claim 1, the rapid-prototyping technique being selected from ink-jet printing, 3d-printing, multi jet plotting, robo-casting, electrophoretic deposition, fused deposition modelling, selective laser sintering or melting, laminated object manufacturing, stereolithography, photostereolithography or combinations thereof.

3. The process according to claim 1, the rapid-prototyping technique comprising a printing or plotting step.

4. The process according to claim 1, the rapid-prototyping technique comprising the steps of providing a layer of a surface coated powder, applying a composition comprising a liquid through a nozzle to at least one section of the layer of the surface coated powder.

5. The process according to claim 1, the first heating step according to step (a) being conducted at a temperature which causes the material of Part B to partially sinter.

6. The process according to claim 1, the second heating step according to step (d) being conducted at a temperature which causes the material of Part B to fully sinter.

7. The process according to claim 1, the fusing composition comprising a liquid and a glass or glass ceramic powder.

8. The process according to claim 1, characterized by at least one of the following features:
the first heating step according to step (a) being conducted in a temperature range from about 300 to about 500° C.;
the second heating step according to step (d) being conducted in a temperature range from about 700 to about 1050° C.

* * * * *